United States Patent
Akervall et al.

(10) Patent No.: US 11,419,752 B2
(45) Date of Patent: *Aug. 23, 2022

(54) CUSTOM-FORMABLE NIGHT GRINDING APPLIANCE AND METHOD OF USE

(71) Applicant: Akervall Technologies, Inc., Saline, MI (US)

(72) Inventors: Jan Akervall, Saline, MI (US);
Charlotte Akervall, Saline, MI (US);
Johann W. Schwank, Saline, MI (US)

(73) Assignee: Akervall Technologies, Inc., Saline, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/369,516

(22) Filed: Jul. 7, 2021

(65) Prior Publication Data

US 2021/0361472 A1 Nov. 25, 2021

Related U.S. Application Data

(63) Continuation of application No. 17/179,791, filed on Feb. 19, 2021, which is a continuation of application
(Continued)

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ..... A61M 16/0488–0495; A61M 16/04; A61F 5/56–566; A61F 5/566; A61F 2005/563;
(Continued)

(56) References Cited

U.S. PATENT DOCUMENTS

| 4,374,690 A | 2/1983 | Canterino et al. |
| 4,537,689 A | 8/1985 | Morrow et al. |

(Continued)

FOREIGN PATENT DOCUMENTS

| BR | PI0605444-7 A | 7/2008 |
| BR | PI0901237-0 A2 | 12/2010 |

(Continued)

OTHER PUBLICATIONS

Jansen, Jeffrey A., Plastics—It's All About Molecular Structure, Sep. 2016, Plastics Engineering, p. 31 (Year: 2016).*
(Continued)

*Primary Examiner* — Michelle J Lee
(74) *Attorney, Agent, or Firm* — Marshall & Melhorn, LLC

(57) ABSTRACT

Disclosed is a dental appliance composed of a thermoplastic polymer with low compressibility, high toughness, and high tensile strength, with a low softening point. The appliance has perforations that enable it to be easily custom-fitted by the user or a health professional. The appliance begins as an unformed dental tray that is significantly thinner than existing dental appliances. Once fitted, the dental appliance provides superior protection against damage to the enamel of the teeth and abrasion of the teeth due to bruxism or other mechanism leading to biomechanical wear of dental surfaces. The perforations facilitate the custom-fitting process by allowing the user to suck air through the perforations, thus applying a negative pressure between the material and the teeth while the material is still soft and pliable.

8 Claims, 4 Drawing Sheets

Related U.S. Application Data

No. 13/894,469, filed on May 15, 2013, now Pat. No. 10,945,874.

(60) Provisional application No. 61/647,093, filed on May 15, 2012.

(58) Field of Classification Search
CPC ............ A63B 71/085; A63B 2071/086; A63B 71/08–10; A63B 2071/088; A61C 7/08; A61C 19/063; A61C 19/066; A61C 19/06–066

See application file for complete search history.

(56) References Cited

U.S. PATENT DOCUMENTS

| | | | |
|---|---|---|---|
| 4,838,283 A | 6/1989 | Lee, Jr. | |
| 4,995,404 A | 2/1991 | Nemir | |
| 5,163,840 A | 11/1992 | Bourke | |
| 5,190,051 A | 3/1993 | Wilson | |
| 5,313,960 A | 5/1994 | Tomasi | |
| 5,490,520 A | 2/1996 | Schaefer et al. | |
| 5,499,633 A | 3/1996 | Fenton | |
| 5,586,562 A | 12/1996 | Matz | |
| 5,666,973 A | 9/1997 | Walter | |
| 5,678,993 A | 10/1997 | Jeffer et al. | |
| 5,692,523 A | 12/1997 | Croll et al. | |
| 5,823,193 A | 10/1998 | Singer et al. | |
| 5,876,199 A | 3/1999 | Bergersen | |
| 5,934,907 A | 8/1999 | Marshall | |
| 6,036,487 A | 3/2000 | Westerman | |
| 6,079,977 A * | 6/2000 | Persichetti | A61C 9/0006 433/41 |
| 6,080,923 A | 6/2000 | Austin | |
| 6,109,266 A | 8/2000 | Turchetti | |
| 6,117,092 A | 9/2000 | Weinstein et al. | |
| 6,241,518 B1 | 6/2001 | Sullivan | |
| 6,295,988 B1 | 10/2001 | Sue | |
| 6,302,100 B1 | 10/2001 | Yoshida | |
| D504,744 S | 5/2005 | Hidalgo et al. | |
| 7,004,756 B2 | 2/2006 | Anderson | |
| 7,047,978 B2 | 5/2006 | Zuk | |
| 7,404,404 B2 | 7/2008 | Lombardi | |
| 7,481,653 B2 | 1/2009 | Anderson | |
| 7,637,262 B2 | 12/2009 | Bailey | |
| 7,891,976 B2 | 2/2011 | Onodera et al. | |
| 8,007,277 B2 | 8/2011 | Fischer et al. | |
| 8,784,100 B2 * | 7/2014 | Marumori | A61C 9/0006 433/37 |
| 2002/0168451 A1 | 11/2002 | O'Donnell Kiely | |
| 2002/0189608 A1 | 12/2002 | Raudenbush | |
| 2003/0075184 A1 | 4/2003 | Persichetti | |
| 2004/0154625 A1 | 8/2004 | Foley | |
| 2005/0034733 A1 | 2/2005 | Liddle et al. | |
| 2005/0113654 A1 | 5/2005 | Weber et al. | |
| 2005/0137514 A1 | 6/2005 | Vito et al. | |
| 2006/0021622 A1 | 2/2006 | Buffington | |
| 2006/0096602 A1 | 5/2006 | Brown | |
| 2007/0023055 A1 | 2/2007 | Roth | |
| 2007/0142498 A1 | 6/2007 | Brennan et al. | |
| 2007/0151567 A1 | 7/2007 | Maurello | |
| 2007/0151568 A1 | 7/2007 | Maurello | |
| 2007/0235039 A1 | 10/2007 | Gottsch | |
| 2008/0044797 A1 | 2/2008 | Bardach et al. | |
| 2008/0066768 A1 | 3/2008 | Dembro | |
| 2008/0115792 A1 | 5/2008 | Burger | |
| 2008/0156324 A1 | 7/2008 | Isenberg et al. | |
| 2008/0199824 A1 | 8/2008 | Hargadon | |
| 2008/0243023 A1 | 10/2008 | Valkhof et al. | |
| 2008/0289638 A1 | 11/2008 | Peters et al. | |
| 2008/0295850 A1 | 12/2008 | Lesniak | |
| 2009/0038624 A1 * | 2/2009 | Akervall | A63B 71/085 128/861 |
| 2009/0056726 A1 | 3/2009 | Bardach et al. | |
| 2009/0075230 A1 | 3/2009 | Bardach et al. | |
| 2009/0087812 A1 | 4/2009 | Andersen | |
| 2009/0130624 A1 | 5/2009 | Sun et al. | |
| 2009/0159089 A1 | 6/2009 | Jansheski | |
| 2009/0165805 A1 | 7/2009 | Syrop et al. | |
| 2009/0277461 A1 | 11/2009 | Gallagher, Jr. et al. | |
| 2010/0009311 A1 | 1/2010 | Pelerin | |
| 2010/0028829 A1 | 2/2010 | Lewis et al. | |
| 2010/0055233 A1 | 3/2010 | Macinnis et al. | |
| 2010/0104998 A1 | 4/2010 | Farnell et al. | |
| 2010/0147315 A1 | 6/2010 | Chodorow | |
| 2010/0206314 A1 | 8/2010 | Brown | |
| 2011/0030704 A1 | 2/2011 | Hanna | |
| 2011/0067710 A1 | 3/2011 | Jansheski et al. | |
| 2011/0067711 A1 | 3/2011 | Jansheski et al. | |
| 2011/0139162 A1 | 6/2011 | Chodorow | |
| 2011/0168186 A1 | 7/2011 | Halstrom | |
| 2011/0174319 A1 | 7/2011 | Busciglio | |
| 2011/0180077 A1 | 7/2011 | Garcia | |
| 2011/0195376 A1 | 8/2011 | Boyd, Sr. | |
| 2011/0230587 A1 | 9/2011 | MacInnis et al. | |
| 2012/0017922 A1 * | 1/2012 | Hirshberg | A63B 71/085 128/861 |
| 2012/0325225 A1 * | 12/2012 | Small | A63B 71/085 128/862 |
| 2013/0299317 A1 | 11/2013 | Moller | |
| 2014/0259330 A1 | 9/2014 | Carbo, Jr. et al. | |
| 2021/0236325 A1 * | 8/2021 | Akervall | A61F 5/566 |

FOREIGN PATENT DOCUMENTS

| | | |
|---|---|---|
| CA | 2591466 A1 | 12/2007 |
| DE | 102010023256 B3 | 11/2011 |
| JP | 2002336286 A | 11/2002 |
| RO | 101093 B1 | 11/1992 |
| WO | 2010074822 A1 | 1/2010 |
| WO | 2010023655 A1 | 4/2010 |
| WO | 2010040050 A2 | 4/2010 |

OTHER PUBLICATIONS

Sigma Aldrich, Polycaprolactone, 2019, https://www.sigmaaldrich.com/catalog/product/aldrich/440744?lang=en&region=US (Year: 2019).*

Sigma Aldrich, Polycaprolactone, 2 019, https://www.sigmaaldrich.com/catalog/product/aldrich/440744?lang=en&region=US.

* cited by examiner

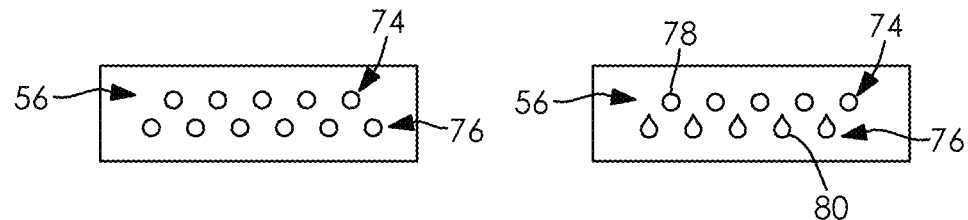
FIG. 7A  FIG. 7B
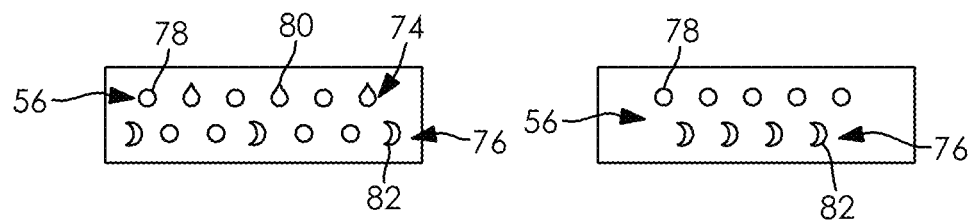
FIG. 7C  FIG. 7D
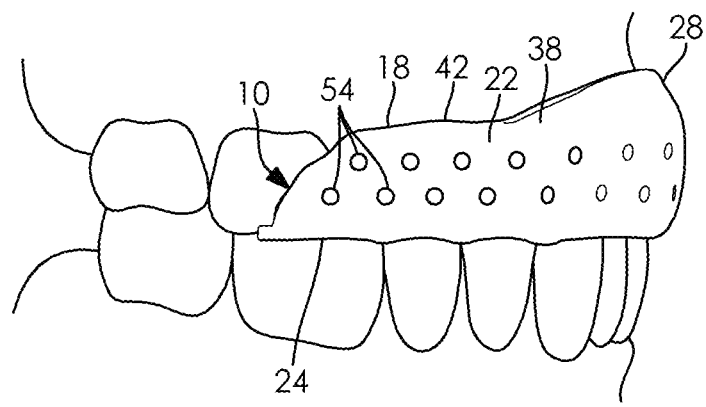
FIG. 8

CUSTOM-FORMABLE NIGHT GRINDING APPLIANCE AND METHOD OF USE

FIELD

The present invention relates generally to night grinding appliances. More particularly, the invention relates to custom-formable night-grinding dental appliances that are thin and have a multiplicity of strategically placed perforations. The perforations facilitate breathing and the flow of saliva while maximizing the protection of teeth with regard to bruxism or other mechanisms leading to biomechanical wear of dental surfaces.

BACKGROUND

Many dental patients suffer from temporomandibular joint disorder (TMD), a condition involving the improper functioning of the jaw and the temporomandibular joint. One of the conditions leading to TMD is bruxism, the subconscious clenching and grinding of teeth that typically occurs during sleep, but that may also occur while the patient is awake. In some cases of bruxism, the forces from jaw movements lead to tooth enamel damage, and over time the exerted excessive pressure can cause damage to the TMJ's articulating surfaces and lead to abrasion of the teeth surfaces. One of the treatments for bruxism is to insert custom-formed dental appliances, also known as "night grinding appliances", or "bruxism protective device" or "mouth guards" to prevent direct contact of the occlusal surfaces of the teeth.

Night grinding appliances or fitted mouth guards are typically prescribed by dentists and custom formed. Typically, the dentist first takes an impression of the patient's teeth, and a cast of the maxillary upper arch is fabricated. Then, a polymeric material, usually an acrylic material is molded over the cast while applying a vacuum. The resulting fitted mouth guard is then trimmed and polished. Alternatively, multiple layers of polymer are laminated together under pressure in an attempt to improve the physical properties of the protective layers. These custom-made fitted mouth guards tend to be very expensive, and require a visit to the dentist, and, in some cases, fabrication in a dental laboratory.

Mouth guards for other uses, such as sports, do not provide protection against shear forces created by bruxism. Sports guards are developed to accommodate single, quick, large forces that are acting substantially normal to the tooth outer surface. Sports guards have no mechanism to contend with constant, low level shear forces from the user's own teeth.

SUMMARY

Described herein is a generally U-shaped dental appliance made of polycaprolactone or other thermoplastic polymer with a low softening point. The appliance is substantially thinner than conventional dental trays and has strategically located perforations. The majority of the perforations are disposed primarily outside of an arc-shaped region associated with a user's bite line. The perforations facilitate breathing and unrestricted flow of saliva. The appliance can easily be heated to its softening point and custom-fitted by a dentist, other health professional, or even by the patient conforming exactly to the contours of the user's dentitions.

The fitted dental appliance provides superior protection against damage to the enamel of the teeth and abrasion of the teeth due to bruxism or other mechanisms leading to biomechanical wear of dental surfaces.

The appliance facilitates the custom-fitting process by allowing the user to suck air and saliva through the perforations, thus applying a negative pressure between the material and the teeth while the material is still soft and pliable. The result is within a short time a conformal fit around every tooth as the material hardens, thus enabling a user or health professional to create a final product that rivals the quality and fit of an appliance made by dental laboratories using dentist made impressions.

The appliance has a periphery including a plurality of lobes and cusps to enhance custom fitting by allowing the softened material to envelop the teeth without buckling.

After fitting to the patient's dentitions, the fitted appliance cools to ambient temperature and contracts slightly, thus conforming even better to the contours of the user's dentitions, and thereby preventing the appliance from getting dislodged or falling out during sleep.

The appliance covers only the teeth and not the gum line on the labial side and the palate on the lingual side, in order to not cause discomfort, irritation of the gums, gagging, or inhibited breathing and saliva flow.

BRIEF DESCRIPTION OF THE DRAWINGS

The features of the subject appliance will be better understood in the context of the detailed description, in conjunction with the drawings.

FIG. 7a depicts one embodiment of a formed appliance with circular perforations.

FIG. 7b depicts another embodiment of a formed appliance with circular and teardrop perforations.

FIG. 7c depicts another embodiment of a formed appliance with half moon and teardrop perforations.

FIG. 7d depicts another embodiment of a formed appliance with half moon perforations.

FIG. 8 shows one embodiment of the formed appliance on the dentitions of a user.

DETAILED DESCRIPTION

It is to be understood that the device may assume various alternative orientations and step sequences, except where expressly specified to the contrary. It is also to be understood that the specific devices and processes illustrated in the attached drawings, and described in the following specification are simply exemplary embodiments of the concepts defined in the appended claims. Hence, specific dimensions, directions or other physical characteristics relating to the embodiments mentioned herein are not limited unless required in the claims.

Figure 4:
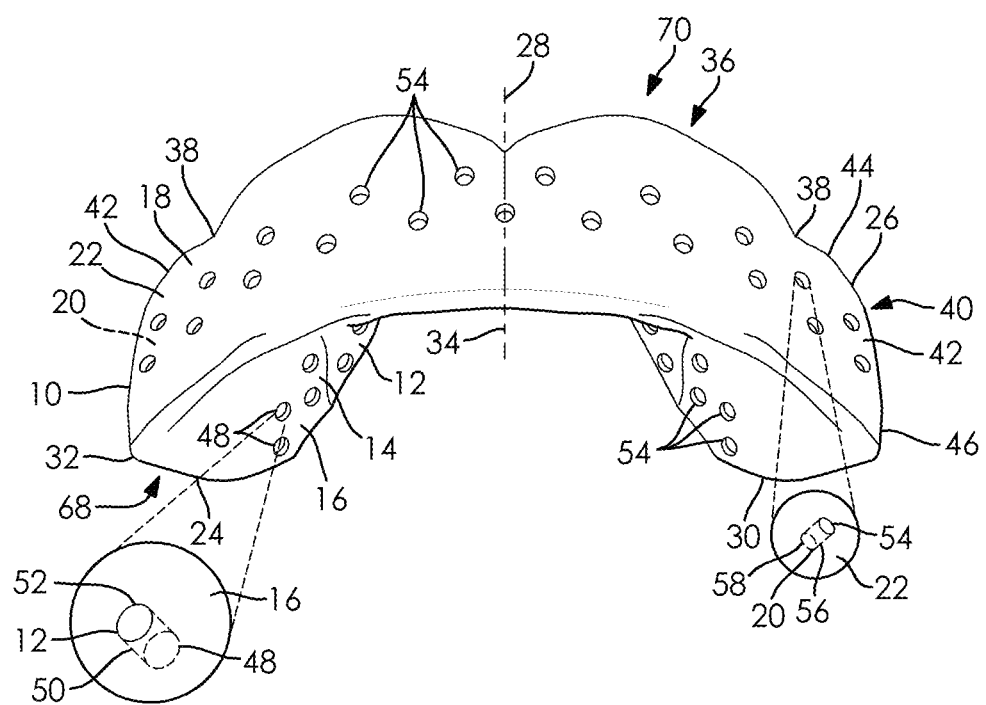
FIG. 4 shows a frontal view of the fitted appliance.
Figure 5:
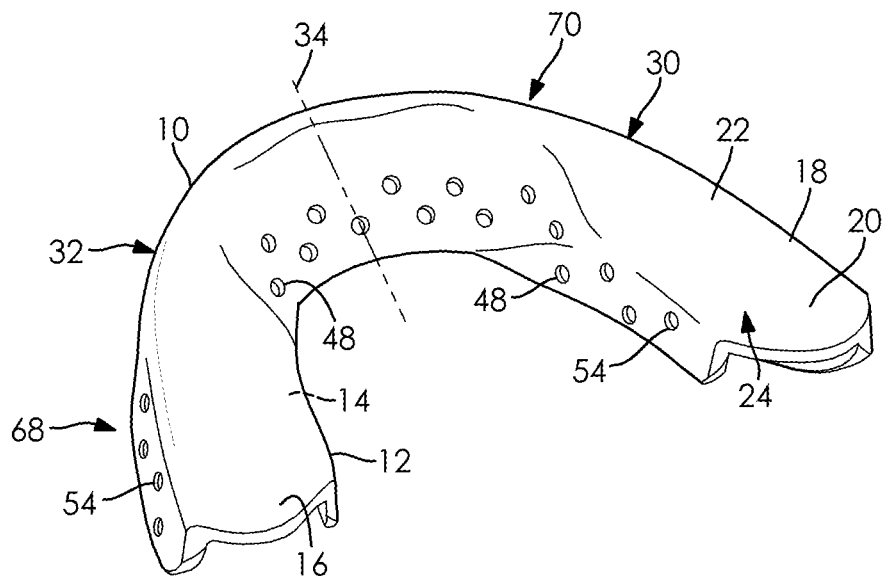
FIG. 5 shows a bottom view of the fitted appliance depicting a lower surface of the appliance that is in contact with the dental surfaces.
Figure 6:
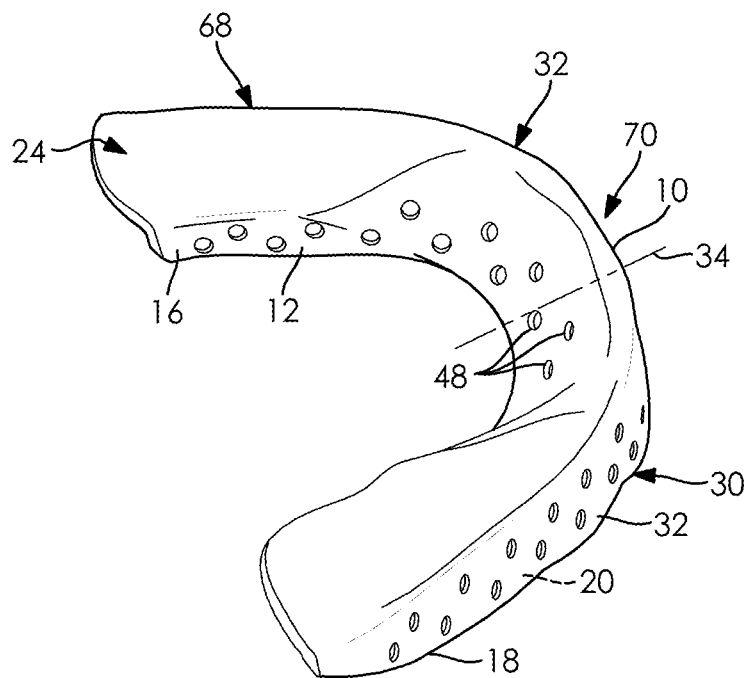
FIG. 6 shows another bottom view of the formed appliance.

Turning now to FIG. 4-6, one embodiment of a mouth guard 10 is depicted. The mouth guard 10 has an inner upstanding wall 12 with an inner surface 14 and an outer surface 16. The two surfaces 14, 16 are generally parallel one another. The guard 10 also has an outer upstanding wall 18 with an inner surface 20 and an outer surface 22. The two surfaces 20, 22 are generally parallel one another. The inner upstanding wall 12 and the outer upstanding wall 18 are connected at their base portions with a U-shaped occlusal line portion 24 to form a U-shaped cross section. The walls 12, 18 of the guard 10 and the occlusal line portion 24 are unitarily formed as one piece. The occlusal line portion 24 is the part of the device that covers the bite line—the surface of the protected dentition that comes in contact with the surface of the dentition on the other jaw when the individual bites down during grinding or clenching. The occlusal line portion 24 can also be appreciated from FIG. 8. The bite line is adapted to receive lateral shearing forces from teeth.

Although the guard 10 may have an upper edge portion 26 of the outer upstanding wall 18 that is relatively straight, in the preferred embodiment a number of small lobes and cusps are located in the outer upstanding wall 18. The lobes and cusps are used to enhance the custom fitting process of the guard 10 to the user's teeth by allowing the softened guard material to adapt to any shape of the user's dentitions during the fitting process. As shown in FIG. 4, the upper edge portion 26 of the outer upstanding wall 18 is provided with at least one cusp. A first cusp 28 is provided between a right half 30 and a left half 32 on a centerline 34 at a forward portion 36 of the outer upstanding wall 18. The guard 10 is symmetric about the centerline 34.

Preferably, a second cusp 38 is provided on the upper edge portion 26 of the outer upstanding wall 18 as well. In the depicted embodiment, the second cusp 38 is provided at a rearward portion 40 of the outer upstanding wall 18. The second cusp 38 is positioned so that it is located between the user's incisors and molars (see also FIG. 8). A lobe 42 formed between points 44 and 46. Lobes 42 and cusps 28, 38 are not depicted on the inner upstanding wall 12 but they may be used on this wall 12 as well.

A cusp 28, 38 is defined as an indentation of the wall 18 of the mouth guard 10, and a lobe 42 is defined as a protruding portion of the wall 18 of the guard 10. Without such cusps 28, 38 and lobes 42, a guard 10 that has been softened to mold against a user's teeth tends to fold or buckle when the guard 10 is wrapped around teeth and gums during fitting. This is especially the case if the curvature and shape of the dentitions are uneven. If such folding occurs when the material hardens during the fitting process, the fitted mouth guard 10 may become uncomfortable to wear, irritating the inside of the lip, and compliance to wear it may decrease. Thanks to these cusps 28, 38 and lobes 42 the final result is a conformally fitted mouth guard 10 that has an outer upstanding wall 18 and an inner upstanding wall 12 both without folds and irregularities and that is extremely comfortable. Another effect of such cusps 28, 38 and lobes 42 is that shear forces to the fitted mouth guard 10, as applied from the lower jaw during grinding, are dissipated away from the occlusal line portion 24, and up towards these cusps 28, 38 and lobes 42, thereby decreasing the negative effect of grinding on the dental surfaces.

Multiphysics computer simulation analysis has shown that the cusps 28, 38, representing singular points on the curvature of the fitted mouth guard 10, act as zones where stresses in the material are concentrated and energy is dissipated, adsorbing and dissipating forces from high impact areas, i.e. the occlusal line portion 24. When shear forces are applied to the fitted mouth guard 10 during grinding or clenching of teeth, a deformation wave front travels though the walls 12, 18 and crests at a cusp 28 and/or 38. This directs the impact energy away from the dentition and concentrates it harmlessly in the cusp 28 and/or 38.

As shown in FIGS. 3A, 4-6, a plurality of openings 48 are located in the inner upstanding wall outer surface 16. The openings 48 connect with a plurality of perforations 50 extending through to the inner upstanding wall 12. The perforations 50 connect with a plurality of exits 52 in the inner upstanding wall inner surface 14.

As also shown in FIGS. 4-6, a plurality of openings 54 are located in the outer upstanding wall outer surface 22. The openings 54 connect with a plurality of perforations 56 extending through the outer upstanding wall 18. The perforations 56 connect with to a plurality of exits 58 in the outer upstanding wall inner surface 20.

The strategically placed perforations 50, 56 in the guard 10 distribute the forces from clenched teeth more evenly and prevent abrasion of the teeth. The perforations 50, 56 increase the ability of the guard 10 to dissipate energy produced during grinding and clenching of teeth by redirecting the forces generated when teeth are clenched and dissipating the energy by temporarily distorting their shape.

As shown in FIGS. 3a, and 4-6, the openings 48, 54 and exits 52, 58 maybe circular in shape and the perforations 50, 56 may be cylindrical. The openings 48, 54, exits 52, 58, and perforations 50, 56 temporarily deform from circles into ovals in the region where a grinding and/or clenching force is applied, as schematically depicted in FIG. 3b.

Figure 3A:
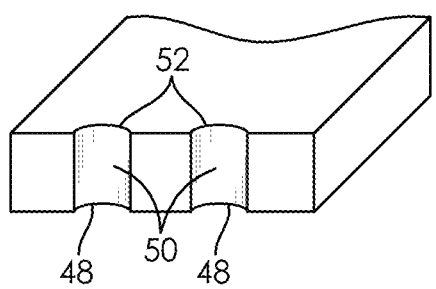
FIG. 3A is a schematic cross section of two adjacent perforations before the application of grinding forces and FIG. 3B is a schematic cross section of the same two adjacent perforations during the application of grinding forces, illustrating how the shape of the perforations changes during application of grinding forces.
Figure 3B:
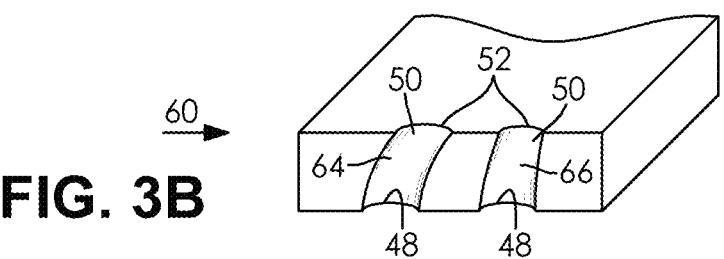

FIGS. 3a and 3b, depict two openings 48, exits 52 and corresponding perforations 50 in the inner upstanding wall 12. A shear force 60, which is applied during grinding, travels along the outer surface 16 (in this example) as a wave. The wave encounters a first perforation 64, which becomes temporarily deformed by the wave. The wave deforms the first perforation 64, which has a circular cross-section, into a perforation with an oval cross-section, which expends some of the energy of the wave. The guard 10 in which the perforation 64 is located maintains a constant volume. Thus, a second perforation 66, which is proximate the first perforation 64, gets compressed to account for the deformation of the first perforation 64. The combination of perforation 64 deformation and the compression of an adjacent perforation 66 acts to absorb the laterally moving shear force in the guard 10. The amount of compression of an adjacent perforation 66 is a function of the amount of deformation caused by the first perforation 64. It can be appreciated that the deformation and compression occurs across many perforations simultaneously in the guard 10.

Based on the foregoing, it can be appreciated that a shear force generated at a rear portion 68 of the guard 10 can be dissipated before it reaches a forward portion 70 of the guard 10 thus causing no distortion in the forward portion 70 perforations.

The perforations 50, 56 are placed in the walls 12, 18 to maximize the tensile strength of the guard 10 without exposing any of the protected dental surfaces to the unprotected teeth on the opposite jaw. The location of the perforations 50, 56 also optimizes saliva flow around the dentitions, which improves comfort.

The perforations 50, 56 improve comfort, i.e. improve breathing and decrease drooling, i.e. the flow of saliva outside the mouth. Breathing is improved since the perforations 50, 56 allow the guard 10 to be thinner and thus take up less space in the mouth. Drooling is decreased since saliva can be sucked straight through the perforations 50, 56 in the guard 10. Drooling is a common problem with conventional dental devices and a major reason for poor compliance to use them. The optimized saliva flow in the current invention that enables the user to suck saliva straight through the guard 10, thus avoiding saliva accumulation around it, mimics the natural sucking and swallowing of saliva an individual does automatically during sleep.

Figure 2:
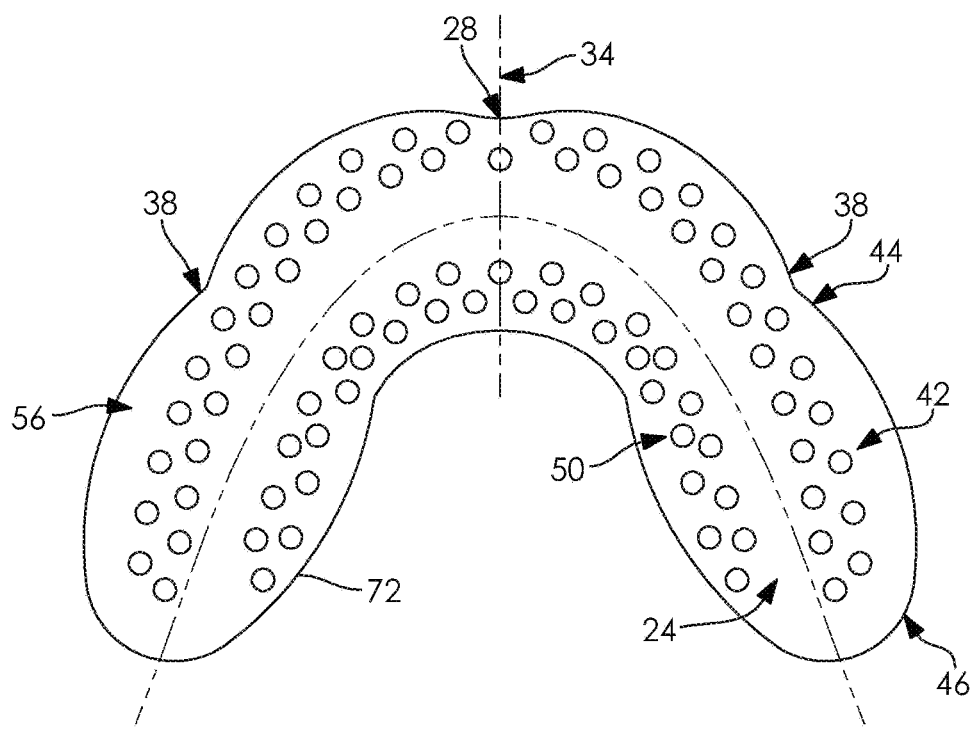
FIG. 2 is a schematic illustration of an unformed tray with strategically placed perforations.

The perforations 50, 56 also improve the fitting procedure. The fitting procedure begins by taking the tray 72 depicted in FIG. 2. The tray 72 is heated, such as by hot water, microwave energy, or the like. Upon application of heat, the tray 72 becomes malleable. The heated tray 72 is put into the user's mouth and against the occlusal line of one set of teeth, such as the top set of teeth.

The perforations 50, 56 allow the user to suck saliva and air through the perforations 50, 56 during the fitting process. This creates a slight vacuum between the softened guard 10 and the dentitions thus attracting the softened material to the dental surfaces and molding it perfectly around the contours of every tooth. The perforations 50, 56 allow the user to suck the softened appliance down onto the dental surface without having to apply any external mechanical pressure. The result is a perfect fit around every individual tooth, no matter the shape or relative location of an individual tooth. Upon cooling, the material retains the shape obtained during the molding process. This overcomes a major problem with conventional fitted mouth guards, where the user has to press the fingers onto the lips from the outside to form the softened fitted mouth guard to the teeth, with generally poor results.

The perforations 50, 56 can be manufactured in a variety of shapes, sizes, and directions through the unformed tray 72, but are typically in the range of 1-2 mm in diameter and shaped as cylindrical, straight, horizontal channels penetrating the walls 12, 18 of the formed guard 10. The location, shape, and direction of these perforations 50, 56 may vary depending on demands on saliva flow, since saliva flow is not uniform throughout the oral cavity. For instance, the saliva flow is higher close to the ducts of the Parotid and submandibular saliva glands, located in the buccal mucosa and in the floor of the mouth. The location of these salivary glands ducts correspond to the rear portion 68 of the fitted guard 10 (Parotid glands) and the inner wall in the midline (Submandibular glands), and the perforations 50, 56 could be bigger in these locations to compensate for greater saliva flow. The perforations 50, 56 may form first and second rows of a first plurality of perforations arranged in two parallel rows adjacent said outer edge portion, as well as first and second rows of a second plurality of perforations arranged in two parallel rows adjacent an inner edge portion, and wherein said first and second rows of said first plurality of perforations extend at a substantially constant distance from said first and second rows of said second plurality of perforations.

Since perforations 50, 56 have been proven to increase the ability of the material to dissipate energy produced during grinding and clenching of teeth by temporarily deforming the cylindrical shape of the perforations 50, 56, a wide variety of the number of perforations 50, 56 and of their exact locations and directions in the material can be used. The present invention can be used on upper as well as lower teeth to improve protection.

The location, size and shape of the perforations 50, 56 are arranged in special patterns that are optimized to dissipate the shear forces applied to the grinding guard by the teeth of the user suffering from bruxism. Enhanced absorption and dissipation of shear forces can be achieved by strategically placing perforations 50, 56 having complex shapes such as tear drop shapes or half-moon shapes, as illustrated in FIG. 7a-d. In some cases, nonsymmetrical perforations, whose shapes are not symmetrical to the laterally traveling shear force wave, are preferable for their ability to absorb and dissipate shear forces.

It is preferred that at least two perforations 50, 56 are located adjacent one another and that the perforations 50, 56 have different shapes. By way of example, a guard 10 might have a circular perforation directly adjacent a teardrop perforation. Preferably, adjacent means that the adjacent perforations are no more than 1-2 perforation diameters away from one another with no intervening structure. This close relationship of perforations is preferred because it allows them to be in force transmitting communication with one another. In one embodiment, the distance between perforations is less than approximately 3 mm and preferably between approximately 1-2 mm.

FIG. 7a depicts one embodiment where two rows of perforations are provided. These perforations 56 are from the outer upstanding wall 18. A first upper row 74 is above a second lower row 76 wherein the perforations 56 in the respective rows are laterally offset from one another and do not overlap. In this embodiment, the perforations 56 in both rows are circular/cylindrical.

FIG. 7b depicts another embodiment where two rows of perforations are provided. A first upper row 74 is above a second lower row 76 wherein the perforations 56 in the respective rows are laterally offset from one another and do not overlap. The perforations in the first row 74 are circular/cylindrical 78; the perforations in the second row 76 are a teardrop shape 80.

FIG. 7c depicts another embodiment where two rows of perforations are provided. A first upper row 74 is above a second lower row 76 wherein the perforations 56 in the respective rows are laterally offset from one another and do not overlap. The perforations in the first row 74 are a combination of circular/cylindrical 78 and tear dropped shaped 80; the perforations in the second row 76 are a combination of half moon shape 82 and circular/cylindrical 78.

FIG. 7d depicts another embodiment where two rows of perforations are provided. A first upper row 74 is above a second lower row 76 wherein the perforations in the respective rows are laterally offset from one another and do not overlap. The perforations in the first row 74 are circular/cylindrical 78; the perforations in the second row 76 are a half moon shape 82.

Based on the foregoing, it can be appreciated that guards 10 can be highly customized to individual bruxism issues of a user. The location, size and shape of perforations can be tailored to the specific type and severity of bruxism experienced by a user.

The shapes, sizes, and exact location of these perforations are determined by multiphysics computer simulations. These multiphysics computer simulations allow to determine the optimum pattern distribution and perforation shapes that allow the guard 10 to deform in such a way that the shear forces applied during grinding are directed into distortions of the perforation shapes in a lateral direction, thereby dissipating energy and protecting the underlying teeth. This permits the appliance to dissipate shear forces by deformation of selected perforations in grinding guard regions that experience shear forces, while maintaining the remaining perforations unaltered. This feature preserves the excellent fit of the grinding guard 10 even under severe bruxism conditions. It is important to note that this mechanism of energy dissipation is fundamentally different than the principles of operation of prior art mouth guards where cylindrical perforations were used to dissipate vertically applied compressive forces. Here, horizontal shear forces are redirected to change the shape of the perforations, a fundamentally different energy absorption mechanism made possible by the special shape of the perforations.

Dental appliances 10 according to this invention are made from a material that is considerably tougher than conventional stock boil and bite appliances, typically made of ethyl vinyl acetate (EVA). The increased toughness of the material improves its ability to absorb energy and its resistance to damage when stressed during clenching and grinding of teeth.

Figure 1:
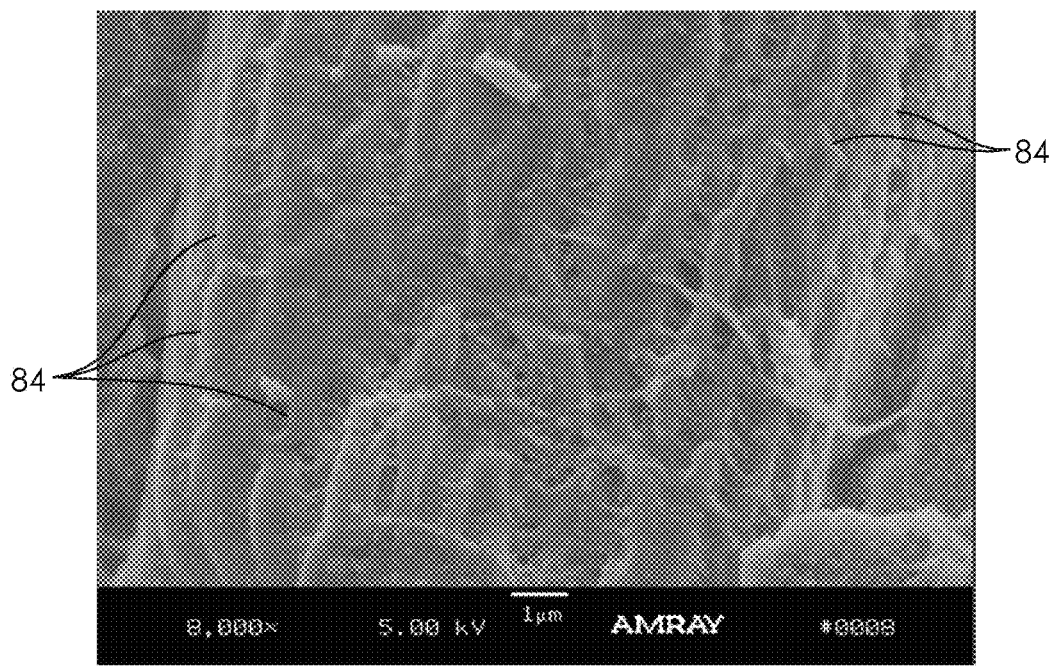
FIG. 1 is a scanning electron micrograph of an unformed tray taken at 8,000× magnification, showing the interwoven strands of the polymer imparting high abrasion resistance.

The material used in this invention is substantially less compressible than the materials used in conventional boil and bite appliances. Preferably, the material is substantially incompressible and substantially constant volume. By way of example, the material may be such as polycaprolactone or other thermoplastic polymers. The mouth guard may be constructed of randomly distributed, randomly oriented interwoven strands of polycaprolactone molecules of random shapes and sizes to increase abrasion resistance of said mouth guard (FIG. 1). According to a multiphysics computer simulation, the material in the current invention deforms only 1.4% under a static load of 2 MPa in comparison to 35% for EVA used in conventional appliances. The less a dental device compresses under impact the less it "caves in". This means that the impact forces dissipate laterally over the device rather than being transferred through the material to the underlying teeth. Better dissipation of forces increases the protection of the dental surfaces. Since compression of the current invention is only 1/25 of conventional dental devices, the transferred forces to the teeth are just a fraction of those in conventional devices, and the degree of protection of the dental surfaces by the current invention is significantly better. Furthermore, less compression results in less permanent deformation of the material itself, which increases its durability. The decreased deformation maintains the excellent conformal fit of the appliance during clenching of teeth and prevents dislodging of the appliance from the dentitions.

Conventional, EVA based appliances need to be about 4 mm thick to provide adequate protection. Thanks to the superior properties of the material in the current invention, a thickness of on average 1.6 mm (range 1.0-2.5 mm) is sufficient to provide adequate protection of the dentitions against abrasion during grinding of teeth. The thinner a night grinding fitted mouth guard 10 is the more comfortable it is, which in turn is important for compliance to use the guard. Bulkier dental device tend to cause gagging. Furthermore, a thinner fitted mouth guard 10 is easier to fit around individual teeth, especially when perforations and the pliability of the current material allows custom fitting to any surface.

The unformed tray 72 may have a uniform thickness, however, when it is fitted the thickness of the appliance may vary. For example, the thickness of the fitted guard 10 may vary in different areas between 1.0 and 1.8 mm when the unformed tray thickness is approximately 1.6 mm. The varying thickness may occur in different areas of the unformed tray to provide increased comfort to the user. Furthermore, the unformed tray 72 may be deliberately made thicker in specific areas where dental abrasion is suspected to occur. This can be accomplished by starting from an unformed tray 72 that has regions of different thickness. For example, the material covering the bite line could be made thicker uniformly or only in specific areas, such as the molar region.

In the preferred embodiments the appliance according to the invention is based on a thermo-plastic polymer with low compressibility. The polymer softens when heated to temperatures above 50° C., allowing it to be conformally fitted to the dentitions. The physical properties of this thermoplastic polymer, such as compressibility, toughness, tensile strength, pliability, and melting point can be adjusted by synthesizing the polymer with different molecular weight distributions (with mean molecular weight in the range of 20,000-80,000), or by incorporating nano-particles and other materials like bentonite clay nanoparticles modified by surfactants such as Stepantex SP-90, to get additional benefits, e.g. increased tensile strength, lower melting temperature, etc. In the preferred embodiment, the polymer is highly abrasion resistant thanks to its structure that contains interwoven strands 84 of polymer, as shown in a magnified scanning electron microscope image (FIG. 1). Since these strands 84 are interwoven and extend deep into the material, they will not easily be pulled out or removed from the material during grinding of teeth, thereby making the appliance more abrasion resistant.

The shape of the unformed tray 72 facilitates the fitting of the softened material by being wide enough to cover all teeth and wrap around them, and by being narrow enough not to cause pressure on the teeth when the fitted mouth guard 10 cools off and contracts around the teeth. In contrast to athletic fitted mouth guards, night grinding fitted mouth guards are used for 6-10 hours straight, and therefore need to be extremely comfortable to guarantee compliance to use them during an entire night's sleep. The carefully designed shape, with cusps 28, 38 and lobes 42 prevents the material from folding when the soft material is molded up against the teeth. The width of the dental unformed tray has also been carefully designed to cover the curved occlusal line portion 24 with solid material without perforations and still allow the user to mold the material up on the inside and outside of each tooth. This design will make sure that the fitted device grips around the teeth and does not fall out during sleep, and at the same time not extend up to the gum line, which is uncomfortable, nor to the hard palate on the inside, which can create gagging. It extends back to the molars, just enough to avoid contact between lower and upper dentitions, but it is short enough to avoid unnecessary gagging. The thinness and the exact design of the unformed dental tray 72 and the location of the perforations 50, 56 allow the material to mold conformally around any uneven surface of the teeth. FIG. 3 shows an example of a fitted appliance.

Due to the ease with which the material can be formed and manipulated, the user can fit the mouth guard 10 on site or at home without assistance of health professionals. Fitting is superior due to the distinct properties of the polymer (thin and pliable at moderate temperatures), and to the design of the unformed dental tray 72 with strategically placed perforations 50, 56, as described above, and lobes 42 and cusps 28, 38 as described above. These properties permit the user to place and fit the heated, softened material over the dentition through a rapid process wherein the material is sucked onto the teeth. In particular, the perforations 50, 56 enhance the effect of the suctioning by allowing the user to create a negative pressure between the teeth and the material, thus sucking the material down to every irregularity of the teeth. Thanks to the perforations 50, 56 in the guard 10, the suctioning maneuver creates a minimal dead space between the material and the teeth, thus leading to a perfect, conformal fit. Without such perforations 50, 56, conformal fitting cannot be done since not enough negative pressure can be built up between a solid material and the dentition. This is reflected in the instructions of conventional fitted mouth guards, where the user is directed to apply downward mechanical pressure on the material, from outside with the fingers, to force the material to come closer to the teeth.

Polymer-based guard 10 according to this invention are inexpensive and disposable thereby improving oral hygiene. Users can move their jaws in any way without risking the guard 10 becoming dislodged.

The guard 10 can be re-shaped to optimize fitting by re-heating to the softening point and repeating the fitting. The superior fit of the guard 10 also results in the need for less material on the inside of the teeth, which in turn reduces gagging and improves comfort.

Users of the inventive guard 10 can breathe more easily. There is more room in the mouth since the guard 10 is considerably thinner than prior art dental appliances, and air can also move freely though the perforations.

In accordance with the provisions of the patent statutes, the present device has been described in what is considered to represent its preferred embodiments. However, it should be noted that the device can be practiced otherwise than as specifically illustrated and described without departing from its spirit or scope.

We claim:

1. A mouth guard, comprising:
a first surface and an opposite second surface, said surfaces being substantially planar and defining a substantially constant thickness between them;
a first plurality of perforations extending entirely through said first surface to said second surface, said first plurality of perforations having a first row and a second row, wherein perforations in said first and second rows are laterally offset;
a second plurality of perforations extending entirely through said first surface to said second surface, said second plurality of perforations having a first row and a second row, wherein perforations in said first and second rows are laterally offset,
a U-shaped bite line separating said first and second rows of said first plurality of perforations from said first and second rows of said second plurality of perforations, wherein said first and second rows of said first and second plurality of perforations extend in a U-shape through the substantially planar first and second surfaces along each side of the U-shaped bite line,
wherein said first plurality of perforations or said bite line are adapted to extend to a region for at least one molar on said first surface,
wherein individual perforations of said first and second plurality of perforations extend spaced from one another continuously from a first rear portion on said first surface to a second rear portion on said first surface,
wherein said bite line is adapted to receive lateral shearing forces from teeth,
wherein said first and second plurality of perforations are adapted to dissipate the shearing forces.

2. The mouth guard of claim 1, further comprising a plurality of cusps on an outer edge portion of a perimeter and a plurality of lobes on said outer edge portion, wherein at least one of the plurality of cusps is located between at least two of the plurality of lobes, wherein said at least one cusp is adapted to dissipate the shearing forces.

3. The mouth guard of claim 2, wherein said first and second rows of said first plurality of perforations are arranged in two parallel rows adjacent said outer edge portion, wherein said first and second rows of said second plurality of perforations are arranged in two parallel rows adjacent an inner edge portion, and wherein said first and second rows of said first plurality of perforations extend at a substantially constant distance from said first and second rows of said second plurality of perforations, wherein said inner edge portion has two lobes.

4. The mouth guard of claim 1, wherein said mouth guard is constructed of randomly distributed, randomly oriented interwoven strands of polycaprolactone molecules of random shapes and sizes to increase abrasion resistance of said mouth guard.

5. The mouth guard of claim 1, wherein individual perforations of said first and second pluralities of perforations have a circular cross section.

6. The mouth guard of claim 1, wherein individual perforations of the first and second plurality of perforations are spaced from one another by a distance of approximately a perforation diameter away from an adjacent perforation.

7. The mouth guard of claim 1, wherein said mouth guard is formed of a substantially incompressible, constant volume material.

8. The mouth guard of claim 1, wherein there are a greater number of perforations in said first plurality of perforations compared with said second plurality of perforations.

* * * * *